United States Patent
Wei et al.

(10) Patent No.: US 11,279,813 B2
(45) Date of Patent: Mar. 22, 2022

(54) PVC PLASTICIZERS AND METHODS FOR MAKING THEREOF

(71) Applicant: KRATON POLYMERS LLC, Houston, TX (US)

(72) Inventors: Xiangyun Wei, Houston, TX (US); Jason Tian, Houston, TX (US); H. Jerrold Miller, Savannah, GA (US); Jos H. M. Lange, Almere (NL)

(73) Assignee: KRATON POLYMERS LLC, Houston, TX (US)

( * ) Notice: Subject to any disclaimer, the term of this patent is extended or adjusted under 35 U.S.C. 154(b) by 265 days.

(21) Appl. No.: 16/515,498

(22) Filed: Jul. 18, 2019

(65) Prior Publication Data

US 2020/0040160 A1    Feb. 6, 2020

Related U.S. Application Data

(60) Provisional application No. 62/714,055, filed on Aug. 2, 2018.

(51) Int. Cl.
*C08K 5/357* (2006.01)
*C08J 3/20* (2006.01)
*C08F 14/06* (2006.01)
*C07D 265/30* (2006.01)

(52) U.S. Cl.
CPC ............ *C08K 5/357* (2013.01); *C07D 265/30* (2013.01); *C08F 14/06* (2013.01); *C08J 3/203* (2013.01)

(58) Field of Classification Search
CPC ....... C08K 5/357; C07D 265/30; C08F 14/06; C08J 3/203
See application file for complete search history.

(56) References Cited

U.S. PATENT DOCUMENTS

| | | | |
|---|---|---|---|
| 2,541,584 A | 2/1951 | Jacoby et al. | |
| 3,250,635 A | 5/1966 | Magne et al. | |
| 3,291,629 A | 12/1966 | Magne et al. | |
| 3,301,798 A | 1/1967 | Waterman et al. | |
| 3,379,551 A | 4/1968 | Magne et al. | |
| 3,385,813 A | 5/1968 | Magne et al. | |
| 3,519,661 A | 7/1970 | Mod et al. | |
| 7,411,012 B2 | 8/2008 | Kaytan | |

FOREIGN PATENT DOCUMENTS

WO    2019-143782 A1    7/2019

OTHER PUBLICATIONS

Bailey et al., Preparation of some mono- and diester of N,N-distributed Amides and Their Evaluation as Plasticizers. Journal of the American Oil Chemists' Society vol. 55, 1978, pp. 459-462 (Year: 1978).*

Magne et al., The Plasticizing Characteristics of Some Fatty Acid Morpholides and Morpholide-Hydrocarbon Extender Blends, J. Am. Oil Chemistry 1968 vol. 45, 567-570 (Year: 1968).*

Bailey, A.V., et al. Preparation of Some Mono- and Diesters of N,N-Distributed Amides and Their Evaluation as Plasticizers. Journal of the American Oil Chemists' Society. vol. 55, 459-462, Year: 1978.

Bonnet, M., et al. Flexidone—A New Class of Innovative PVC Plasticizers, Recent Advances in Plasticizers, Dr. Mohammad Luqman (Ed.), ISBN: 978-953-51-0363-9, InTech, Available from: http://www.intechopen.com/books/recent-advances-in-plasticizers/flexidone-a-new-class-of-innovative-pvcplasticizers.

Magne, Frank C., et al. Fatty Acid Morpholides as Plasticizers for Vinyl Chlorida Resins. II. The Morpholides of Selectivity Hydrogenated and of Expoxidized Cottonseed Fatty Acids. J Am Oil Chem Soc. 1961 38, 291-293.

Magne, Frank C., et al. The Plasticizing Characteristics of Some Fatty Acid Morpholides and Morpholide-Hydrocarbon Extender Blends. J Am Oil Chem 1968 45, 567-570.

Mod, R.R., et al. Preparation and Plasticizing Characteristics of Some N,N-Distributed Amides of Erucic and Crambe Acids. I & EC Product Research and Development, vol. 8, No. 2, 1999, 176-182.

* cited by examiner

*Primary Examiner* — Robert D Harlan

(57) ABSTRACT

A plasticized PVC composition free of phthalate and having low color is disclosed. The composition comprises a morpholide plasticizer prepared from a fatty acid selected from a tall oil fatty acid, a tall oil fatty acid monomer derived therefrom, and mixtures thereof. The fatty acid has a total carbon footprint of <95% of the total carbon footprint of a fatty acid obtained from a vegetable oil. The morpholide is prepared from the reaction of a tall oil fatty acid with morpholine in the presence of a catalyst.

17 Claims, No Drawings

PVC PLASTICIZERS AND METHODS FOR MAKING THEREOF

RELATED APPLICATIONS

This application claims priority from U.S. Application No. 62/714,055, with a filing date of Aug. 2, 2018, the disclosures of which is incorporated herein by reference.

FIELD

The present disclosure relates to polyvinyl chloride (PVC) plasticizer compositions derived from fatty acids having a low carbon footprint, such as tall oil fatty acids, and methods for making the compositions.

BACKGROUND

Plasticizers are added to materials to modify their physical properties, increase the plasticity, i.e., a non-reversible deformation of a material in response to an applied force, or to increase the fluidity. Commercial plasticizers are typically based on non-renewable petrochemical chemical feedstocks, like phthalic acid, terephthalic acid, or benzoic acid. Plasticizers are commonly divided into phthalate and non-phthalate plasticizers. With some prior art plasticizers, e.g., DEHP (bis(2-ethylhexyl) phthalate), the composition has good plasticizing efficiency, but migration rate is too high to be used in high temperature applications. The petrochemical-based, non-phthalate plasticizer, TOTM (trioctyl trimellitate), has a relatively low migration rate suitable for high temperature applications, but poor plasticizing efficiency.

Cyclic monoamides, e.g., those derived from pyrrolidone, have been used as plasticizers. Several classes of bio-plasticizers have been developed, like sebacates, citrates, succinates, isosorbides, and plasticizers derived from castor oil, epoxidized soybean oil, etc. These bio-plasticizers are esters and generally do not offer optimal PVC compatibility. Further, they can lead to unfavorable properties due to leakage by diffusion.

There is still a need for plasticized PVC polymer compositions that have a low carbon footprint, are free of phthalate, and have improved properties that balance good plasticizing efficiency with low migration tendency.

SUMMARY

One aspect of the disclosure is a fatty acid morpholide composition comprising a reaction product of a morpholine compound and a fatty acid, wherein the fatty acid has a total carbon footprint of <95% of the total carbon footprint of a fatty acid obtained from a vegetable oil, or alternatively a low carbon footprint of less than about 500 grams $CO_2$/kg fatty acid, or less than about 200 grams $CO_2$/kg fatty acid.

Another aspect of the disclosure is a morpholide composition, which is a reaction product of a morpholine compound and a fatty acid selected from a tall oil fatty acid (TOFA), a tall oil fatty acid monomer derived therefrom (TOFA monomer), and mixtures thereof; wherein the fatty acid comprises 20-55 wt. % of oleic acid and 20-55 wt. % of linoleic acid; and optionally up to 15 wt. % of linolenic acid. The fatty acid has a total carbon footprint of <95% of the total carbon footprint of a fatty acid obtained from a vegetable oil or alternatively an average carbon footprint of less than 500 gram $CO_2$ equivalents per kg of the fatty acid. The morpholide composition has a Gardner color (neat) of less than about 3.

In another aspect, the disclosure provides a polymer composition comprising polymers, such as polyvinyl chloride (PVC), and the above morpholide compositions that are used as plasticizers.

Another aspect of the disclosure is a method of preparing a plasticized PVC composition free of phthalate, which comprises blending and compounding the above morpholide compositions with PVC and one or more polymer stabilizers and antioxidants.

In a still another aspect, a method of preparing a plasticizer composition free of phthalate is disclosed. The method comprises forming a mixture comprising a morpholine compound, a catalyst, and a fatty acid, where the fatty acid is selected from a TOFA, a TOFA monomer derived therefrom, and mixtures thereof. The fatty acid comprises about 20-55 wt. % of oleic acid and about 20-55 wt. % of linoleic acid; and optionally up to 15 wt. % of linolenic acid; and has a total carbon footprint of <95% of the total carbon footprint of a fatty acid obtained from a vegetable oil or alternatively an average carbon footprint of less than 500 gram $CO_2$ equivalents per kg of the fatty acid.

DESCRIPTION

The following terms will have the following meanings unless otherwise indicated.

"Free of phthalate" means no phthalate is intentionally added.

"Carbon footprint" refers to the total greenhouse gas emission caused directly and indirectly by a product, process, or event. Carbon footprint can be measured in tonnes of carbon oxide equivalent.

"Low carbon footprint" or "reduced carbon footprint" means having <95%, or <92%, or <90%, or <80%, or <70%, or <50%, or <30%, or <20% of the carbon footprint of a substitute product, process, or event. For example, a tall oil fatty acid (TOFA) has a reduced carbon footprint, as depending on the sources, as compared to alternatives, e.g., TOFA may have 10% of emissions compared to a substitute soybean oil (https://www.forchem.com/forchem/low_carbon_solutions), or at least five times lower than a vegetable oil substitute made from soybeans, sunflowers, rapeseed and oleic mixtures (see http://www.kraton.com/products/pdf/Oleochemcials_web_final.pdf).

"Low carbon footprint" fatty acid means a fatty acid having an average carbon footprint of less than 500 gram $CO_2$ equivalents per kg of the fatty acid, preferably less than 200 gram $CO_2$ equivalents per kg of the fatty acid.

"Exudation" is used in the context of a plasticizer component included in a polymer composition, particularly a PVC composition. The term means a measure of the compatibility of a plasticizer component with a polymer matrix, such as, for example, PVC. Exudation of a plasticizer can be evaluated by placing a film sample between two pieces of tissue paper. The combined system (sample+paper) is then stored at room temperature for 48 hrs. The increase in weight of the paper after this duration gives a measure of the exudation of the plasticizer.

Viscosity is determined according to ASTM D2196 with spindle No. 21.

"Acid number" (or "neutralization number" or "acidity") refers to acid value determined by ASTM D465-05 (2010) test method, and is expressed as the mass of potassium hydroxide (KOH) in milligrams that is required to neutralize one gram of the morpholide compositions disclosed herein.

"Amine value" (or "amine number") refers to the milligrams of potassium hydroxide (KOH) having a basicity equivalent to that of 1 gram of the morpholide compositions disclosed herein. It can be determined colorimetrically by titrating a solution of the morpholide sample with dilute hydrochloric acid in isopropanol solvent.

Tensile strength and elongation are measured as per ASTM D882-12 test method. Hardness is measured per ASTM D2240-15 test method. Yellowness index (YI) is measured per ASTM E313-15e1 test method.

The disclosure relates to the preparation and use of a morpholide composition derived from a fatty acid having a low carbon footprint. Such fatty acids have a fraction of the carbon footprint of vegetable acids, such as soybean, palm, sunflower, and peanut acids.

The disclosure also relates to the preparation and use of a morpholide composition prepared from TOFA, a TOFA monomer derived therefrom, or mixtures thereof, for use as a plasticizer with a balanced performance of good plasticizing efficiency and minimal migration when incorporated into a polymer, such as for example, PVC.

Tall Oil Fatty Acid (TOFA):

The TOFA is a TOFA distillate component having one or more carboxylic acid groups that undergo an amidation reaction with a morpholine compound to form amide bonds.

In one embodiment, the TOFA contains more than 80 wt. % of C18 carboxylic acids. In another embodiment, the TOFA comprises C18 long chain carboxylic acids, comprising one or more carbon-carbon double bonds, and relatively low cloud point and pour point. Examples of the C18 long chain carboxylic acids include stearic acid (a C18 saturated carboxylic acid), oleic acid (a C18 mono-unsaturated carboxylic acid), linoleic acid (a C18 di-unsaturated carboxylic acid), and alpha-linolenic acid (a C18 tri-unsaturated carboxylic acid). The TOFA may also contain minor fractions (<0.5 wt. %) of palmitic acid (a C16 saturated carboxylic acid) and saturated and unsaturated carboxylic acids having more than 18 carbon atoms.

In one embodiment, the carboxylic acids include, but are not limited, to the those having a carbon chain length of 16-20, such as palmitic acid, stearic acid, oleic acid, linoleic acid, elaidic acid, alpha-linolenic acid, arachidic acid, 14-methylhexadecanoic acid, octadecadienoic acid, 11,14-ericosadienoic acid, cis-5,cis-11,cis-14-ericosatrienoic acid, 8(9), 15-isopimaradien-18-oic acid, 2α-[2'(m-isopropylphenyl)ethyl]-1β, 3α-dimethylcyclohexanecarboxylic acid, 8(9), 15-pimaradien-18-oic acid, 2β-[2'(m-Isopropylphenyl) ethyl]-1β/3α-dimethylcyclohexanecarboxylic acid, 8(14), 15-pimaradien-18-oic acid, 7(8)/15-pimaradien-18-oic acid, 8,13-Abietadien-18-oic acid, palustric acid, 7,15-isopimaradien-18-oic acid, isopimaric acid, dihydroabietic acid, abietic acid, 8,11,13-abietadien-18-oic acid, and 8(14),13(15)-abietadien-18-oic acid.

In another embodiment, the carboxylic acids include varying amounts of other vegetable acids, e.g., canola acids, castor acids, coconut acids, cottonseed acids, linseed acids, peanut acids, rapeseed acids (low erucic acid), rapeseed acids (high erucic acid), safflower acids, soybean acids, and sunflower acids.

In one embodiment, the TOFA comprises 20-55 wt. % of oleic acid and 20-55 wt. % of linoleic acid, and optionally up to 15 wt. % of linolenic acid. In another embodiment, the TOFA optionally comprises up to 15 wt. % of a sum of alpha-linolenic acid and pinolenic acid, and 1 to 4 wt. % of saturated fatty acid(s), as determined by the ACQM 022 test method. In another embodiment, the TOFA contains 0.1-5 wt. % of C-20 resin acid(s). In one embodiment, the TOFA has an oleic acid level of 32 wt. %, a conjugated linoleic acid and linoleic acid (also referred to as (9Z,12Z)-octadeca-9, 12-dienoic acid) combined content of 50 wt. %, an alpha-linolenic acid content of 12 wt. %, a saturated fatty acids content of 2%, an acid number of 197 mg KOH/g (AQCM 001), and an iodine number of 154 cg I/g (AQCM 009), and a pour point of −15° C. (AQCM 060). In another embodiment, the TOFA has an acid number of 194 mg KOH/g, an iodine number of 125 cg I/g, and a color of 4.5 Gardner (neat) (AQCM 002). In yet another embodiment, the TOFA has an acid number of 196 mg KOH/g, an iodine number of 125 cg I/g, and a color of 3.0 Gardner (neat). In yet another embodiment, the TOFA component is characterized as having a reduced footprint, i.e., a total carbon footprint of <95% of the total carbon footprint of a fatty acid obtained from a vegetable oil.

Tall oil distillate predominantly contains TOFA. TOFA suitable for preparing the morpholide derivative can be obtained by refining crude tall oil grades. In one embodiment, the TOFA distillate has a pour point (° C.) from −35° C. to 30° C. as determined by ACQM 060 test method. In another embodiment, the TOFA distillate has a pour point (° C.) from −25° C. to 15° C. In yet another embodiment, the TOFA distillate has a pour point of −15° C.

In another embodiment, a TOFA-derived chemical composition, such as a tall oil fatty acid monomer (also referred to as "TOFA monomer") is also used to prepare the morpholide composition. The TOFA monomer is present in the monomeric fraction formed during the acidic clay catalyzed polymerization of TOFA. In this polymerization process, typically conducted at high temperatures, the olefinic fatty acids undergo a variety of chemical reactions, including isomerizations and intermolecular addition reactions, to form a mixture of dimerized and polymerized fatty acids, as well as a unique mixture of monomeric fatty acids. The monomeric fatty acids fraction is separated from the polymerization product by separation methods, such as distillation, and is commonly known in the art as "monomer" or "monomer acid" or "monomer fatty acid" (CAS Registry Number 68955-98-6).

TOFA monomer is typically a mixture of branched-, aromatic, cyclic, and straight chain fatty acids, which can be saturated or unsaturated, wherein the olefinic double bonds in the unsaturated fatty acids can have cis- or trans-configurations. The predominant acid in TOFA monomer is the so-called "iso-oleic acid", which is actually a mixture of linear, branched and cyclic C-18 mono-unsaturated fatty acids. In an example, the TOFA monomer contains both saturated and unsaturated C-18 fatty acids, where iso-oleic acids are present as the major component and polyunsaturated fatty acids are present at a low level. Further, the example TOFA monomer has an acid number of 174 mg KOH/g (AQCM 001), a Gardner color (neat) of 6.1 (AQCM 002), an iodine number of 75 cg I/g (AQCM 009).

In some embodiments, the TOFA monomer is a chemically modified TOFA, such as iso-oleic acid, and their refined or hydrogenated fractions, such as iso-stearic acid and related branched, saturated or partly saturated C-18 carboxylic acid compositions. In one embodiment, the TOFA monomer is a mixture of branched and straight chain fatty acids which is formed during the dimerization reaction of TOFA and obtained from the resulting reaction mixture. In another embodiment, the TOFA monomer acid contains both saturated and unsaturated C-18 fatty acids, with branched chain iso-oleic acids constituting the main portion, and virtually no polyunsaturated fatty acids.

Iodine number is generally used to indicate the degree of unsaturation of an oil, fat, or wax. The TOFA or TOFA monomer component has an iodine number in centigrams of iodine/gram of TOFA ranging from 60 to 180, from 110-170, or from 125-155 cg I/g, as determined by ACQM 009.

Morpholine Component:

To form the morpholide compositions, a morpholine compound is employed for reaction with the TOFA. In one embodiment, morpholine, ($O(CH_2CH_2)_2NH$) is used. In another embodiment, the morpholine compound is selected from the group consisting of morpholine, 2-methylmorpholine, 2,6-dimethylmorpholine, 2,2-dimethylmorpholine, 3-methylmorpholine, or mixtures thereof.

Morpholine can be produced by dehydration of diethanolamine with sulfuric acid. Another method involves reaction of diethylene glycol with ammonia in the presence of a catalyst such as Raney nickel.

Optional Component:

In one embodiment, the reaction mixture forming the morpholide composition further comprises a rosin-containing material, e.g., a tall oil rosin, a gum rosin or a combination thereof, in an amount of less than 15 wt. % (relative to the total weight of the morpholide plasticizer composition). Non-limiting examples of rosin-containing materials include SYLVAROS™ products from Kraton Corporation.

The morpholide compositions may further comprise a scavenging agent such as, for example, an acid scavenging agent such as a substituted or an unsubstituted glycidyl ester. The scavenging agents reduce formation of color bodies.

Modified Forms of TOFA Morpholide:

The low carbon footprint fatty acid morpholides, including the TOFA morpholide compositions, can have varying amounts of residual unsaturation predominantly derived from the unsaturated fatty acid components, such as oleic acid, linoleic acid and linolenic acid. These unsaturation sites can be partially or completely removed using various chemical conversions to provide morpholides having little to no residual unsaturation. Examples include, but are not limited to, epoxidation, hydrogenation, chlorination, bromination, hydrochlorination, and hydrobromination. Partial or complete removal of unsaturation improves the thermal stability of the morpholides and also lowers the color of the product. Plasticizer compositions incorporating such modified morpholides can have even lower color or can have higher thermal stability, for producing low color plasticizer polymer compositions, such as a plasticized PVC composition.

Method for Making the Morpholide Composition:

The morpholide composition can be made in an amidation reaction, where morpholine or a substituted morpholine reacts with a fatty acid, with elimination of water. Any amidation catalyst known in the art can be used. An acid catalyst is generally used to aid the forward reaction. Examples include the phosphorus acids, such as orthophosphoric acid ($H_3PO_4$), metaphosphoric acid ($HPO_3$), phosphorous acid ($H_3PO_3$), and hypophosphorous acid ($H_3PO_2$). Other types of phosphorous acids, such as pyrophosphoric acid ($H_4P_2O_7$), triphosphoric acid ($H_5P_3O_{10}$), and trimetaphosphoric acid ($H_3P_3O_9$) may also be used as catalysts. In one embodiment, hypophosporous acid is used as the catalyst for forming the morpholide compositions. Still other examples of amidation catalysts include phosphoric acid, 2-(2'-pyridyl)ethylphosphonic acid (PEPA) and its diethyl ester (DPEP), sodium hypophosphite, phenylphosphonic anhydride, phenylphosphonic acid, phenylphosphinic acid, arylboronic acid and other boron containing chemical entities, Lewis acids like $FeCl_3$, dehydrating agents such as molecular sieves, phosphonium salts and carbodiimides.

The amidation reaction is conducted by heating the reaction mixture to a temperature required for forming the morpholide composition. In an embodiment, the reaction temperature is greater than 200° C. Water is formed as a by-product during the amidation reaction and is preferably removed during the reaction as a vapor, for example, via a stream of inert purge gas, such as nitrogen. Prior to, or after the product isolation step, the reaction mixture containing the morpholide product can be treated with a scavenging agent, such as glycidyl ester. Product isolation is achieved by distillation, for example, wiped film evaporation and short path distillation. An antioxidant can be added to the isolated product to stabilize it against oxidative decomposition.

The morpholides can also be synthesized by other methods, such as by reacting the carboxylic acid derivatives of TOFA with a morpholine compound. For example, esters, such as methyl or lower alkyl esters of TOFA can react with the morpholine compound in the presence of a catalyst. An acyl chloride derivative of the TOFA can be reacted with a morpholine in the presence of an organic amine, which acts as a base. Alternatively, an acid anhydride derived from the TOFA can be reacted with an amine to produce the morpholide composition.

The morpholide compositions prepared as described above may still contain residual unsaturation present in the TOFA or the low carbon footprint fatty acid. Such unsaturation can be partially or completely removed using methods described hereinabove.

Plasticizer compositions comprising the above morpholide compositions may contain one or more than one type of morpholides based on structural variations in the morpholine component and/or the TOFA component. The acyl group in the morpholide structure comprises an 18-carbon acyl group. In an embodiment, the plasticizer composition comprises a morpholide composition resulting from reaction of morpholine with a TOFA. In another embodiment, the plasticizer composition comprises a morpholide composition resulting from reaction of a morpholine compound with 2 or more different TOFA monomers. In yet another embodiment, the plasticizer composition comprises a morpholide composition resulting from reaction of morpholine and one or more substituted morpholine compounds with TOFA. In a still another embodiment, the plasticizer composition comprises a morpholide composition resulting from reaction of morpholine and one or more substituted morpholine compounds with TOFA and one or more TOFA monomers.

Properties of the Morpholide Compositions and the Morpholide Plasticizer Compositions:

The morpholide compositions (and plasticizer compositions therefrom) made by the described methods have a Gardner color (neat) of <5, or <3, or <2.

The morpholide compositions have an acid number of less than 12 mg KOH/g; alternatively less than 9 mg KOH/g, alternatively less than 5 mg KOH/g, and alternatively less than 3 mg KOH/g. The morpholides have an amine value of <6 mg KOH/g; or <4 mg KOH/, or <2 mg KOH/g, or <1 mg KOH/g.

The morpholides derived from a fatty acid having a carbon footprint of less than 500 gram $CO_2$ equivalents per kg of the fatty acid, including the TOFA morpholide, have a low tendency to leak, and a low tendency to exudation when included in polymer compositions. This makes them useful for producing polymer compositions, such as those comprising PVC and/or vinyl chloride-vinyl acetate copolymer resin. In such systems, the plasticizer is characterized as being substantially compatible with the PVC and/or vinyl chloride-vinyl acetate copolymer resin.

Industrial Applicability:

The TOFA-based morpholide plasticizers are useful in construction applications, e.g., pipe and profile applications, such as doors and windows. They can also be used for making bottles, non-food packaging, and cards (e.g., bank or membership cards). Other applications include plumbing, electrical cable insulation, imitation leather, signage, phonograph records, flooring, inflatable products, toys, and many applications where they serve to replace rubber.

The TOFA-based morpholide plasticizer can be included in PVC compositions by methods known in the art, e.g., plastisol method, dry blending, compounding, and extrusion. Dry blending is carried out in mixing equipment such as a ribbon blender or a high-speed mixer. In one embodiment, the TOFA-based morpholide plasticizer is incorporated in an amount ranging from 10-90 phr (parts by weight per 100 parts by weight of the PVC resin), and in another embodiment from 10-60 phr. Appropriate amounts of PVC and other required solid ingredients are first blended together, then liquid plasticizer is added to the mixture with stirring. In one example, the dry blend is next processed and extruded or molded into final applications.

In embodiments, the plasticized PVC composition has a yellowness index ($\Delta E$) of 3 or less after aging at 70° C. for 7 days.

EXAMPLES

The following examples are intended to be non-limiting.

Example 1 (E-1)

A morpholide composition is prepared from a reactant mixture comprising 73.4 wt. % of a TOFA (comprising 45-50 wt. % of oleic acid and 40-45 wt. % of linoleic acid), 1 wt. % of catalyst (hypophosphorous acid), and 25.6 wt. % of morpholine.

TOFA and hypophosphorous acid (catalyst) were combined in a reaction flask fitted with a condenser setup to collect the by-product water as a condensate. After purging the reaction flask with nitrogen for 30 minutes to remove oxygen, the mixture was heated to 210° C. at a rate of 100° C./hour. Then morpholine was added sub-surface at a rate of 0.3 wt. % over a period of 100 minutes. After all the morpholine had been added, the temperature was held at 210° C., while the reaction progress was monitored by sampling aliquots of the reaction mixture and measuring their acid value and amine value using titration techniques. When the acid value was less than or equal to 9 mg KOH/g, the reaction mixture was sparged with nitrogen for 1 hour, cooled to 70° C., and treated with 1 wt. % of a glycidyl ester and stirred for 1 hour. Next, the reaction mixture was placed in a wiped film evaporator and heated to 220° C. at a pressure of 100-300 millibar ($1\times10^4$-$3\times10^4$ pascals). The pure morpholide composition was collected as the head cut, cooled to ambient temperature under nitrogen protection, and poured into a storage vessel. To this, 1 wt. % of an anti-oxidant was added and stirred until a homogeneous liquid resulted. The final product was stored in a sealed container at room temperature. The product had a Gardner color (neat) of 0.9, an acid value of 5.6 mg KOH/g, an amine value of 0.0 mg KOH/g, and a viscosity of 40 cPs at 30° C.

Examples (CE-2, E-2, CE-3, E-3)

PVC formulations were prepared using the TOFA morpholide of Example 1, prior art PVC plasticizers (TOTM and DOTP), and other components as shown in Table 1. The blends were processed at temperatures between 175° C. to 205° C.

TABLE 1

| Components | CE-2 | E-2 | E-3 | CE-3 |
|---|---|---|---|---|
| PVC resin (phr) | 100 | 100 | 100 | 100 |
| TOTM trioctyl mellitate (phr) | 55 | 0 | 0 | 0 |
| TOFA morpholide of E-1 (phr) | 0 | 36 | 13 | 0 |
| DOTP dioctyl phthalate (phr) | 0 | 0 | 0 | 20 |
| Filler CaCO₃ | 21 wt. % | 21 wt. % | | |
| Ca/Zn heat stabilizer 1 | Not used | Not used | 1.5 | 1.5 |
| Ca/Zn heat stabilizer 2 | Not used | Not used | 1.5 | 1.5 |
| UV stabilizer | Not used | Not used | 0.4 | 0.4 |

The resulting PVC compound is then compression molded into testing plaques, and then tested for their properties. Table 2 shows the properties of the plasticized PVC compositions. Tensile and elongation data were collected according to ASTM D638. CIEL*a*b* is used for color measurement of PVC plaques, where L* is for the lightness, a* is for green-red component, and b* is for blue-yellow color component. $\Delta E$ is the difference between two colors, and it is calculated according to the following equation:

$$\Delta E = \sqrt{(L^*_2 - L^*_1)^2 + (a^*_2 - a^*_1)^2 + (b^*_2 - b^*_1)^2}$$

In Table 2, initial $\Delta E$ for the Example composition E-2 is the difference in color between the Example and Comparative Example before aging, and aged $\Delta E$ for a given sample is the color difference measured before and after aging for the same sample.

TABLE 2

| Examples | $\Delta E$ | | Hardness Shore A aged | | Elongation (%) | | Tensile (psi) | |
|---|---|---|---|---|---|---|---|---|
| | Initial | Aged | Initial | Aged | Initial | Aged | Initial | Aged |
| CE-2 | 0.0 | 1.6 | 90 | 90 | 194 | Not tested | 2,316 | Not tested |
| E-2 | 6.0 | 3.1 | 90 | 90 | 176 | Not tested | 2,251 | Not tested |
| E-3 | 8.1 | 12.0 | 76 | 76 | 142 | Not tested | 5084 | Not tested |
| CE-3 | 0.0 | 4.3 | 76 | 76 | 180 | Not tested | 5220 | Not tested |

As shown, PVC compositions E-2 and E-3 used 35 wt. % less plasticizer, as compared to compositions having TOTM or DOTP (CE-2 and CE-3). Further, the percent elongation and tensile strength of the plasticized compositions E-2 and E-3 were comparable to those exhibited by the comparative compositions CE-2 and CE-3 comprising TOTM and DOTP, respectively.

Examples without Fillers

Several formulations without fillers are shown in Table 3. The compositions were made on a Brabender, compression molded into testing plaques, and then tested for Shore A hardness. Results show that TOFA morpholide is a more efficient plasticizer than DOTP over wide formulation range.

TABLE 3

|  | CE-4 | E-4 | CE-5 | E-5 | CE-6 | E-6 |
|---|---|---|---|---|---|---|
| PVC | 100 | 100 | 100 | 100 | 100 | 100 |
| DOTP | 80 |  | 60 |  | 40 |  |
| TOFA Morpholide |  | 80 |  | 60 |  | 40 |
| Additives (wt. %) | ~1% | ~1% | ~1% | ~1% | ~1% | ~1% |
| Shore A Hardness | 65 | 62 | 77 | 72 | 88 | 81 |

Examples—Plastisol Formulations

Plastisol compositions containing emulsion PVC were formulated as shown in Table 4, and were then casted and dried. Testing plaques were then cut from the cast sheet, and tested for properties. TOFA morpholide once again gives better plasticizer efficiency than the traditional phthalate PVC as shown in Table 4.

TABLE 4

|  |  | E-7 | CE-7 |
|---|---|---|---|
| PVC Resin P-121 |  | 100 | 100 |
| TOFA Morpholide |  | 65 | — |
| DINP |  | — | 65 |
| Epoxidized soybean oil |  | 3 | 3 |
| Stabilizer |  | 1.5 | 1.5 |
| Viscosity (cps) | Initial | 1620 | 2320 |
| at 2.5 rpm | 1 week | 4000 | 5200 |
| lbs./gallon |  | 9.73 | 9.84 |
| Hardness (Shore A) |  | 72 | 75 |
| Air Release |  | Good | Good |

Examples—Fusion Rate

Compositions as listed in Table 5 were formulated using a Brabender at 180° C. and 50 rpm, then evaluated for fusion rate according to ASTM D-2538. As shown in Table 5, TOFA morpholide not only has better plasticizing efficiency, but also has faster fusion rate.

TABLE 5

|  | CE-8 | E-8 |
|---|---|---|
| CaCO3 (wt. %) | 54% | 54% |
| DOTP (phr) | 58 | — |
| TOFA Morpholide (phr) | — | 45 |
| Other additives (wt. %) | ~1% | ~1% |
| Fusion Time (sec) | 48 | 34 |
| Hardness (Shore A) | 93.8 | 93.7 |
| Tensile (psi) | 1,325 | 1,405 |
| Elongation % | 143 | 166 |
| Tear Strength k lb/in | 0.21 | 0.23 |
| Wt. loss (70° C. 7 days) | 0.25 | 0.22 |

Unless defined otherwise, all technical and scientific terms used herein have the same meanings as commonly understood by one of skill in the art to which the disclosed disclosure belongs. Publications cited herein and the materials for which they are cited are specifically incorporated by reference. The term "comprising" and variations thereof as used herein is used synonymously with the term "including" and variations thereof and are open, non-limiting terms. Although the terms "comprising" and "including" have been used herein to describe various aspects, the terms "consisting essentially of" and "consisting of" can be used in place of "comprising" and "including" to provide for more specific aspects of the disclosure and are also disclosed.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A morpholide composition, comprising a reaction product of a morpholine compound and a fatty acid selected from a tall oil fatty acid, a tall oil fatty acid monomer derived therefrom, and mixtures thereof;
   wherein the fatty acid comprises 20-55 wt. % of oleic acid and 20-55 wt. % of linoleic acid;
   wherein the fatty acid has a total greenhouse emission expressed as $CO_2$ g equivalents per kg of the fatty acid of <95% of the total $CO_2$ g equivalents per kg of a fatty acid obtained from a vegetable oil; and
   wherein the morpholide composition has a Gardner color (neat) of less than 3.

2. The morpholide composition of claim 1, wherein the fatty acid has an average greenhouse emission of less than 500 gram $CO_2$ equivalents per kg of the fatty acid.

3. The morpholide composition of claim 1, wherein the morpholide composition has an acid number of less than 12 mg KOH/g.

4. The morpholide composition of claim 1, wherein the morpholide composition has an amine value of less than 1 mg KOH/g.

5. The morpholide composition of claim 1, wherein the fatty acid is a tall oil fatty acid monomer, and wherein the tall oil fatty acid monomer comprises iso-oleic acid.

6. A plasticizer composition comprising the morpholide composition of claim 1.

7. A plasticized polyvinyl chloride (PVC) composition comprising the plasticizer composition of claim 6.

8. The plasticized PVC composition of claim 7, having a weight loss after 48 hours of less than 1% in an exudation test.

9. The plasticized PVC composition of claim 7, having a yellowness index ΔE of 3 or less after aging at 70° C. for 7 days.

10. A method of preparing a plasticized PVC composition free of phthalate, comprising blending and compounding the morpholide composition of claim 1 with plasticized polyvinyl chloride and one or more polymer stabilizers and antioxidants.

11. A method of preparing a morpholide composition, comprising:
forming a mixture comprising a morpholine compound, a catalyst, and a fatty acid selected from a tall oil fatty acid, a tall oil fatty acid monomer derived therefrom, and mixtures thereof;
wherein the fatty acid comprises 20-55 wt. % of oleic acid and 20-55 wt. % of linoleic acid; and the fatty acid has a total greenhouse emission expressed as $CO_2$ g equivalents per kg of the fatty acid of <95% of the total $CO_2$ g equivalents per kg of a fatty acid obtained from a vegetable oil; and isolating the morpholide composition;
wherein the morpholide composition has a Gardner color (neat) of less than 3.

12. The method of claim 11, wherein the fatty acid has an average greenhouse emission of less than 500 gram $CO_2$ equivalents per kg of the fatty acid.

13. The method of claim 11, wherein the catalyst is hypophosphorous acid.

14. The method of claim 11, further comprising adding a scavenging agent to the isolated morpholide composition.

15. The method of claim 14, wherein the scavenging agent is a substituted or an unsubstituted glycidyl ester.

16. The method of claim 10, wherein said isolating the morpholide composition comprises wiped film evaporation or short path evaporation.

17. The method of claim 10, further comprising a step for reducing residual unsaturation, selected from the group consisting of epoxidation, hydrogenation, bromination, chlorination, hydrochlorination, and hydrobromination.

* * * * *